United States Patent [19]

Neri et al.

[11] Patent Number: 5,218,116

[45] Date of Patent: Jun. 8, 1993

[54] PROCEDURE FOR THE PREPARATION OF NITROXYL RADICALS OF STERICALLY HINDERED AMINES

[75] Inventors: Carlo Neri; Silvestro Costanzi, both of Milan; Rosa M. Riva, Como; Mariangela Angaroni, Varese, all of Italy

[73] Assignee: Enichem Synthesis S.p.A., Palermo, Italy

[21] Appl. No.: 800,039

[22] Filed: Nov. 29, 1991

[30] Foreign Application Priority Data

Nov. 30, 1990 [IT] Italy ................. 22264 A/90

[51] Int. Cl.$^5$ ................. C07D 265/30; C07D 211/02; C07D 209/04; C07D 207/06
[52] U.S. Cl. ................. 544/106; 546/113; 546/184; 546/186; 546/242; 548/490; 548/537; 548/570; 548/542; 548/579
[58] Field of Search ............... 546/184, 242, 186, 113, 546/184, 242, 186, 113; 548/579, 530, 570, 537, 490, 542; 544/106, 173

[56] References Cited

U.S. PATENT DOCUMENTS

| | | | |
|---|---|---|---|
| 2,695,301 | 11/1954 | Blicke | 548/530 |
| 4,201,721 | 5/1980 | Hallgren | 558/268 |
| 4,792,623 | 12/1988 | Sun | 564/315 |

*Primary Examiner*—Mary C. Lee
*Assistant Examiner*—Joseph K. McKane
*Attorney, Agent, or Firm*—Oblon, Spivak, McClelland, Maier & Neustadt

[57] ABSTRACT

Procedure for the preparation of nitroxyl radicals of sterically hindered amines, consisting of the reaction of amines with hydrogen peroxide in the presence of a titanium containing catalyst, particularly in the presence of titanium silicalites.

The catalyst can be recovered at the end of the reaction and recycled.

21 Claims, No Drawings

PROCEDURE FOR THE PREPARATION OF NITROXYL RADICALS OF STERICALLY HINDERED AMINES

The present invention concerns a method for the preparation of stable nitroxyl radicals of sterically hindered amines.

It is known that these radicals are mainly used as stabilizers of organic polymers (P. P. Klemchuk. ACS Symposium, 1985); they are also used as spin labels which can be measured by means of radical detecting equipment.

There are basically two methods of synthesis known in the art, which can be used industrially: the first is based on the oxidation reaction of the above amines with hydrogen peroxide in the presence of catalysts containing tungsten.

The most suitable catalysts for this purpose are phosphotungstic acid and sodium tungstate.

The disadvantages of these methods lie mainly in the impossibility of recycling the catalytic system and in the necessity of washing the reaction products at the end of the reaction to purify them from the catalytic system which could damage their activity.

A method has recently been discovered for obtaining the nitroxyl derivatives of hindered amines (Tetrahedron lit. 29, (37), 4677 (1988)) by making these react with dimethyldioxirane without catalysts. However, even if the yield of nitroxyl radicals is considerable, the process is quite costly due to the fact that a non-commercial product is used.

The aim of the present invention is therefore to overcome the above-mentioned disadvantages of the known procedure.

More specifically, the first aspect of the present patent application concerns a new procedure for the preparation of nitroxyl radicals of sterically hindered amines, which consists in making the amines react with hydrogen peroxide in the presence of a catalyst containing titanium (for example, catalysts suitable for the purpose are titanium bioxides and titanium silicalites).

The proposed method is simple, economical and enables the catalyst to be recovered at the end of the reaction and possibly recycled.

Titanium silicalites were originally considered excellent catalysts in the oxidative processes of olefinic and aromatic hydrocarbons of alkalies and phenols (Perego, Notari 1988 zeolites: Synthesis, Characterization and Application; Catalitica Studies Division, 430 Ferguson Drive; Mountain View, Calif.).

Then oxidation reactions were also carried out of aromatic amines in the presence of zeolites with the formation of diphenyl groups (J. Chem. Soc., Faraday Trans,. 71 1192-1202. (1975)) and oxidation reactions of aniline in the presence of titanium silicalites with the formation of azoxybenzene ( (A. Fujimura, M. Oguri, Y. Kano, M. Uemura); Cat. Symp. acta—Hokkaido Un. Japan—July 1989)).

Also known is the oxidation reaction of secondary aliphatic amines with hydrogen peroxide in the presence of titanium silicalites with the formation of hydroxylamine derivatives (E.P.A. 88 117950.1).

In this case, the oxidation products of the secondary amines are hydroxylamines.

However, the surprising discovery has been made that by using the sterically hindered amines as substrates, the reaction products are just those stable nitroxyl radicals that are used as stabilizers.

The oxidation reaction, subject of the present invention, is obtained with high yields, in accordance with the following reactions.

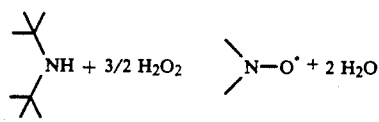

Examples of sterically hindered amines suitable for the synthesis of nitroxyl radicals according to the synthesis procedure of the present invention are:

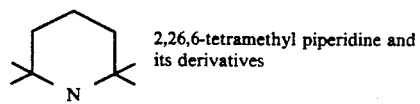

2,26,6-tetramethyl piperidine and its derivatives

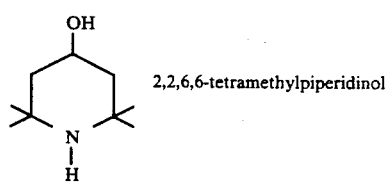

2,2,6,6-tetramethylpiperidinol

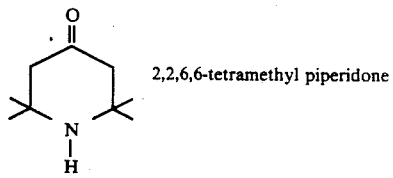

2,2,6,6-tetramethyl piperidone

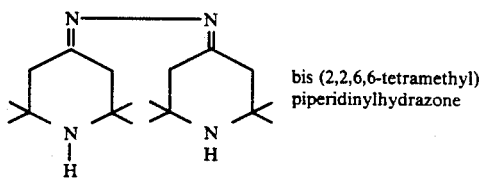

bis (2,2,6,6-tetramethyl) piperidinylhydrazone

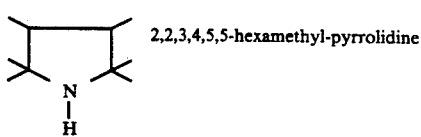

2,2,3,4,5,5-hexamethyl-pyrrolidine

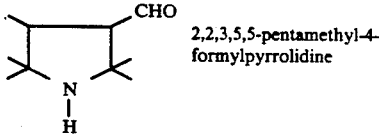

2,2,3,5,5-pentamethyl-4-formylpyrrolidine

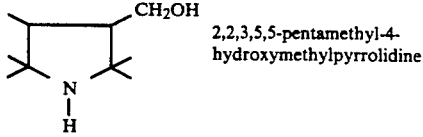

2,2,3,5,5-pentamethyl-4-hydroxymethylpyrrolidine

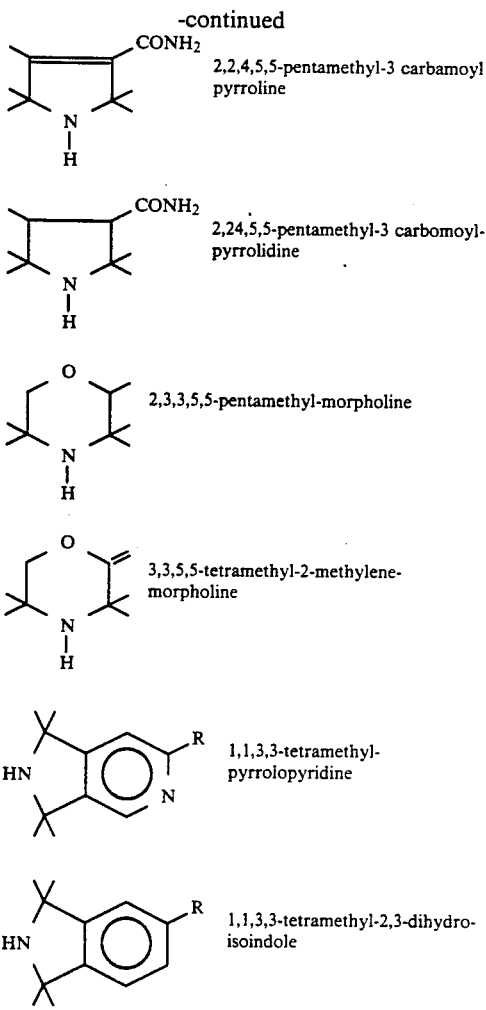

- 2,2,4,5,5-pentamethyl-3 carbamoyl pyrroline
- 2,24,5,5-pentamethyl-3 carbomoyl-pyrrolidine
- 2,3,3,5,5-pentamethyl-morpholine
- 3,3,5,5-tetramethyl-2-methylene-morpholine
- 1,1,3,3-tetramethyl-pyrrolopyridine
- 1,1,3,3-tetramethyl-2,3-dihydro-isoindole where R is H or a linear or branched alkyl radical containing 1–6 carbon atoms.

With respect to the synthesis reaction of the nitroxyl radicals, this can be carried out by adding hydrogen peroxide to the mixture composed of the catalyst and secondary amine and which is kept under stirring.

The reaction can be carried out with or without a solvent. Either water or an organic solvent can be used as solvents.

Solvents suitable for the purpose are ketones such as acetone or cyclohexanone, halogenated aliphatic hydrocarbons such as dichloroethane or methylene chloride or other similar products, as for example, alcohols such as methyl alcohol or terbutylic alcohol.

It is also possible to use mixtures of the above alcohols with water.

The reaction can be carried out at a temperature ranging from 20° to 100° C. even if it is preferable to heat the reaction mixture to a temperature of between 40° and 80° C. to accelerate the kinetics and improve the yield.

The quantity of hydrogen peroxide used in the oxidation reactions of the secondary amines varies from 2 to 4 times the quantity in moles of the substrate.

The quantity of zeolitic catalyst normally used varies from 1 to 10% by weight of the weight of the amine even if, from the point of view of kinetics and cost of the catalyst, it is preferable to use quantities ranging from 4% to 7% of the weight of the amine.

As a zeolitic synthetic catalyst containing titanium, it is convenient to use a titanium silicalite corresponding to the general formula $$X\, TiO_2\, (1-X)\, SiO_2$$

X ranging from 0.0001 to 0.04, preferably between 0.01 and 0.025.

This kind of catalyst and a method for its preparation are described in GB-B-2071071 (U.S. Pat. No. 4,410,105) the contents of which are included for reference.

Titanium silicalites with a definite structure are just as valid as oxidation catalysts. For example titanium silicalite with the ZSM-5 structure (Ti-ZSM-5) is particularly suitable.

The synthesis method of titanium silicalite generally includes, however, the preparation of a reaction mixture containing sources of silicon oxide, titanium oxide and possibly sources of an alkaline oxide, a nitro organic base and water, having a composition, expressed in terms of the molar ratios of the reagents, within the following ranges:

| Reagents | Molar ratios | Preferred molar ratios |
|---|---|---|
| $SiO_2/TiO_2$ | 5–200 | 35–65 |
| $OH/SiO_2$ | 0.1–1.0 | 0.3–0.6 |
| $H_2/SiO_2$ | 20–200 | 60–100 |
| $Me/SiO_2$ | 0.0–0.5 | 0 |
| $RN^+/SiO_2$ | 0.1–2.0 | 0.4–1.0 | where Me represents an alkaline ion, preferably chosen from Na and K, and $RN^+$ represents the organic cation deriving from the nitro organic base.

The source of silicon oxide can be a tetralkyl-ortho-silicate, preferably tetraethyl-ortho-silicate, or quite simply a colloidal silica, or, the silicate of an alkaline metal, preferably Na or K.

The source of titanium oxide is a compound of titanium, which can be hydrolized, preferably chosen from $TiCl_4$, $TiOCl_2$ and $Ti(alkoxy)_4$, preferably $Ti(OEt)_4$.

The typical organic base is a hydroxide of tetra-alkylammonium.

For the preparation of the titanium silicalite, the mixture of reagents is submitted to hydrothermal treatment in an autoclave at temperatures ranging from 130° to 200° C., at autogenous pressure and over a period of 6–30 days, until the crystals of the precursor of titanium-silicalite have been formed; these are then separated from the mother solution, carefully washed with water and dried; the precursor of titanium-silicalite thus obtained, and having in its anhydrous state, the following composition:

$$xTiO_2\, (1-x)SiO_2\, 0.04\, (RN^+)_2O$$

is heated, in air, at approximately 550° C. ranging from 1 to 72 hours, in order to completely eliminate the nitro organic base. The titanium-silicalite thus obtained has the above composition.

At the end of the reaction, the catalyst is easily removed by filtration and, as stated previously, can be used again in other reactions with a slight loss of activity causing a decrease in the rate of the reaction.

The yields obtained are generally high and depend on the kind of substrate and its hindrance.

The reaction time varies from 3 to 24 hours.

At the end of the reaction, when the catalyst has been removed by filtration, the product is recovered by extraction with an organic solvent and then usually purified by crystallization.

The following examples are intended to provide a clearer illustration of the present invention without limiting it in any way.

EXAMPLE 1

Preparation of 2.2.6.6.-tetramethyl/piperidinyl N-oxide radical

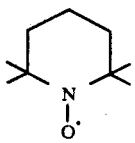

10 g (0.071 moles) of 2,2,6,6-tetramethyl piperidine, 0.7 g of titanium silicalite (TS-1) obtained as described in Example 1 of GB-B-2071071 and 30 cc of methanol are placed in a flask equipped with a thermometer, magnetic stirrer, reflux condenser and drip funnel.

The mixture, under continual stirring, is brought to the reflux temperature of the solvent (65° C.) and a 30% w/w water solution of $H_2O_2$ (32.2 g, 0.284 moles) is slowly added over a period of 1 hour.

The mixture is kept, under stirring, at a temperature of 65° C. for a further 6 hours and the solution is analysed by gas-chromatography every hour.

When the reagent is no longer present, the solution is cooled and the catalyst removed by filtration.

NaCl is added to the filtered solution which is extracted with two 20 cc portions of petroleum ether (boiling temperature 58°–70° C.).

The ether extracts are mixed together, dried on $Na_2SO_4$ and evaporated to remove the solvent.

A small quantity of hexane is then added to the residue which is left to crystallize at a temperature of 0° C.

The crystalline product in needle form, filtered at room temperature, washed with a small quantity 5–10 cm³ of cold hexane and then dried under vacuum, has a bright red colour and a melting point of between 36° and 38° C.

Using the above procedure, 10.5 gr. (94.6% yield) of the product were recovered with the following elementary analysis:

|  | C (%) | H (%) | N (%) |
|---|---|---|---|
| Theoretical | 69.2 | 11.6 | 8.96 |
| Experimental | 69.05 | 11.55 | 9.04 |

EXAMPLES 2-6

Preparation of 2,2,6,6-tetramethylpiperidinyl-N-oxide radical

The following examples demonstrate how the activity of the catalyst varies when it is reused in further reactions.

The same procedure is used as in Example 1 and the catalyst is recycled after filtration.

Table 1 below shows the conversion percentage of 2,2,6,6-tetramethyl-piperidine after 6 hours of reaction at the reflux temperature of the methanol.

TABLE 1

| Examples | No. recycles | Conversion % of 2,2,6,6-tetra-methylpiperidine after 4 h of reaction |
|---|---|---|
| 2 | 0 | 98 |
| 3 | 1 | 92 |
| 4 | 2 | 87 |
| 5 | 3 | 80 |
| 6 | 4 | 65 |

EXAMPLES 7-9

Preparation of 2,2,6,6-tetramethylpiperidinyl N-oxide radical

The following examples show how the conversion varies using different solvents.

The same procedure is used as in Example 1 substituting the methanol solvent with water (Example 7), water-acetone 1:1 (Example 8), ter-butanol (Example 9) in the same volumes (30 cc.).

Table 2 below shows the conversion after 6 hours of reaction determined by gas-chromatography.

TABLE 2

| Examples | T (°C.) | Conversion % after 4 h of reaction |
|---|---|---|
| 7 | 80 | 97 |
| 8 | 60 | 99 |
| 9 | 80 | 95 |

EXAMPLE 10

Preparation of 2,2,6,6-tetramethyl 4 piperidinol N oxide radical

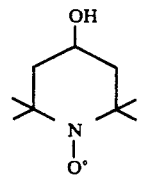

MW 172

15.7 g (0.1 moles) of 2,2,6,6-tetramethylpiperidinol, 0.8 g of titanium silicalite (TS-1) and 40 cc of solvent consisting of a 1:1 volume mixture of water-methanol, are placed in a flask equipped with a thermometer, magnetic stirrer, reflux condenser and drip funnel.

The mixture is heated to 70° C. and 23 g (0.4 m) of 60% w/w $H_2O_2$ are then added over a period of 3 hours.

The reaction mixture is left for 24 hours at the same temperature and the solution analysed by gas-chromatography.

When the catalyst has been filtered, $K_2CO_3$ is added to the solution and then extracted with diethyl ether.

The ether extract is dried on $Na_2SO_4$ and then evaporated.

Hot hexane is added to the residue which is then separated from the 2,2,6,6-tetramethyl piperidinol, crystallized from the hexane, filtered and dried.

The product thus obtained with a 95% yield, is in a red crystalline form with a melting point of 72°–73° C.

EXAMPLES 11-16

Using the same procedure as in Example 10, nitroxyl radicals are obtained which are shown in Table 3 with the corresponding % yields after a reaction in a solvent composed of a 1:1 mixture by weight of water-methanol at a temperature of 70° C.

| Example | Substrate | Product | Yield (%) |
|---|---|---|---|
| 11 | | | 85 |
| 12 | | | 99 |
| 13 | | | 92 |
| 14 | | | 85 |
| 15 | | | 87 |
| 16 | | | 5 | filtration, and recovering the product by extraction with an organic solvent.

3. A process according to claim 1, characterized by the fact that the catalyst containing titanium is a synthetic zeolite corresponding to the general formula

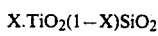

We claim:

1. A process for the preparation of a nitroxyl radical of a sterically hindered amine, comprising reacting a sterically hindered amine with hydrogen peroxide in the presence of a catalyst containing titanium selected from the group consisting of titanium silicalites and synthetic zeolites having the formula

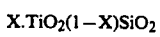

wherein X is a number between 0.0001 and 0.04, wherein said process is carried out either with or without a solvent.

2. A process for the preparation of a nitroxyl radical of a sterically hindered amine, comprising adding hydrogen peroxide, under continual stirring, to a mixture comprising a catalyst, secondary amine, and optionally a solvent, maintaining the mixture under stirring for a time ranging from 3 to 24 hours at a temperature of between 20° and 100° C., removing said catalyst by filtration, and recovering the product by extraction with an organic solvent.

X being a number between 0.01 and 0.025.

4. Procedure according to claim 1, characterized by the fact that the sterically hindered amine is 2,2,6,6-tetramethyl-piperidine

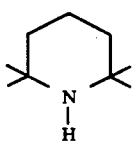

5. A process according to claim 1, characterized by the fact that the sterically hindered amine is 2,2,6,6-tetramethylpiperidinol

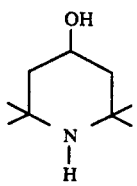

6. A process according to claim 1, characterized by the fact that the sterically hindered amine is 2,2,6,6-tetramethylpiperidone

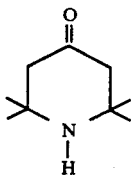

7. A process according to claim 1, characterized by the fact that the sterically hindered amine is bis(2,2,6,6-tetramethyl) piperidinyl-hydrazone

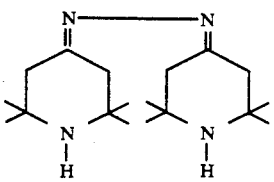

8. A process according to claim 1, characterized by the fact that the sterically hindered amine is 2,2,3,4,5,5-hexamethyl-pyrrolidine

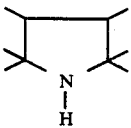

9. A process according to claim 1, characterized by the fact that the sterically hindered amine is 2,2,3,5,5-pentamethyl-4-formylpyrrolidine

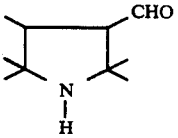

10. A process according to claim 1, characterized by the fact that the sterically hindered amine is 2,2,3,5,5-pentamethyl-4-hydroxymethylpyrrolidine

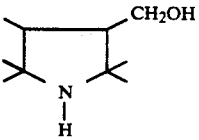

11. A process according to claim 1, characterized by the fact that the sterically hindered amine is 2,2,3,5,5-pentamethyl-4-carbamoyl-pyrrolidine

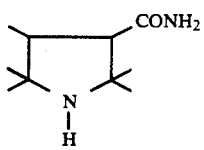

12. A process according to claim 1, characterized by the fact that the sterically hindered amine is 2,2,3,5,5-pentamethyl-4-carbamoyl-pyrroline

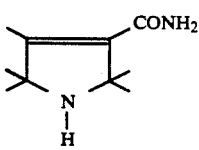

13. A process according to claim 1, characterized by the fact that the sterically hindered amine is 2,3,3,5,5-pentamethyl-morpholine

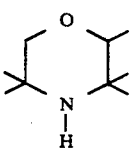

14. A process according to claim 1, characterized by the fact that the sterically hindered amine is 3,3,5,5-tetramethyl-2-methylene-morpholine

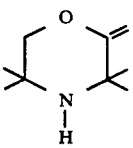

15. A process according to claim 1, characterized by the fact that the sterically hindered amine is 1,1,3,3-tetramethyl-pyrrolopyridine

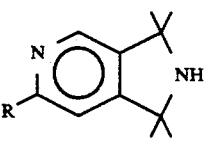

16. A process according to claim 1, characterized by the fact that the sterically hindered amine is 1,1,3,3-tetramethyl-2-dihydro-isoindole

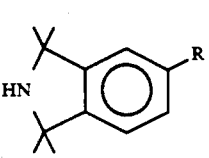

where R is H or a linear or branched alkyl radical containing 1-6 carbon atoms.

17. A process according to claim 1, characterized by the fact that either water or an organic solvent can be used as solvents.

18. A process according to claim 17, characterized by the fact that solvents suitable for the purpose are ketones such as acetone or cyclohexanone, halogenated aliphatic hydrocarbons such dichloroethane or methyl chloride or similar products, as well as methanol, ethanol, propanol and butanol, or alcohol-water mixtures.

19. A process according to claim 2 characterized by the fact that the reaction is carried out at a temperature ranging from 40° to 80° C.

20. A process according to claim 2 characterized by the fact that the quantity of hydrogen peroxide used in the oxidation reactions of the secondary amines ranges from 2 to 4 times the quantity in moles of the substrate.

21. A process according to claim 2 characterized by the fact that the quantity of zeolitic catalyst normally used varies from 1% to 10% of the weight of the amine.

* * * * *